(12) United States Patent
Shtarov et al.

(10) Patent No.: US 8,779,196 B2
(45) Date of Patent: Jul. 15, 2014

(54) POLYFLUOROALKYLSULFONAMIDO ALKYL HALIDE INTERMEDIATE

(75) Inventors: Alexander Borisovich Shtarov, Wilmington, DE (US); Volodymyr B. Pashovych, Bristol, CT (US)

(73) Assignee: E I du Pont de Nemours and Company, Wilmington, DE (US)

( * ) Notice: Subject to any disclaimer, the term of this patent is extended or adjusted under 35 U.S.C. 154(b) by 671 days.

(21) Appl. No.: 13/048,230

(22) Filed: Mar. 15, 2011

(65) Prior Publication Data

US 2011/0237834 A1    Sep. 29, 2011

Related U.S. Application Data

(60) Provisional application No. 61/317,491, filed on Mar. 25, 2010.

(51) Int. Cl.
  *C07C 303/00* (2006.01)
(52) U.S. Cl.
  USPC ............................................................ 564/96
(58) Field of Classification Search
  CPC .................................................... C07C 311/03
  USPC ............................................................ 564/96
  See application file for complete search history.

(56) References Cited

U.S. PATENT DOCUMENTS

| | | | |
|---|---|---|---|
| 3,708,538 | A | 1/1973 | Hahn et al. |
| 3,721,706 | A | 3/1973 | Hoffmann et al. |
| 4,069,158 | A | 1/1978 | Bertocchio et al. |
| 4,296,034 | A | 10/1981 | Bouvet et al. |
| 4,424,133 | A | 1/1984 | Mulligan |
| 4,431,595 | A | 2/1984 | Hashimoto et al. |
| 4,486,391 | A | 12/1984 | Hashimoto |
| 4,826,634 | A | 5/1989 | Baasner et al. |
| 4,836,281 | A | 6/1989 | Robin et al. |
| 4,983,769 | A | 1/1991 | Bertocchio et al. |
| 5,399,756 | A | 3/1995 | Schneider et al. |
| 5,514,493 | A | 5/1996 | Waddell et al. |
| 5,580,847 | A | 12/1996 | Morikawa et al. |
| 6,201,122 | B1 | 3/2001 | Dams |
| 6,960,410 | B2 | 11/2005 | Kim et al. |
| 2001/0001478 | A1 | 5/2001 | Dams et al. |
| 2001/0038949 | A1 | 11/2001 | Hatazaki et al. |
| 2006/0177717 | A1 | 8/2006 | Teasley et al. |
| 2007/0093678 | A1 | 4/2007 | Umemoto et al. |
| 2009/0137831 | A1 | 5/2009 | Rostovtsev |

FOREIGN PATENT DOCUMENTS

| | | |
|---|---|---|
| CN | 1528479 A | 9/2004 |
| DE | 2617746 A1 | 11/1976 |
| EP | 1013311 A1 | 6/2000 |
| EP | 1088814 A1 | 9/2000 |
| GB | 1378984 | 10/1972 |
| JP | 1980146173 A | 11/1980 |
| JP | 1983038569 A | 3/1983 |
| JP | 1983038570 A | 3/1983 |
| JP | 1983038571 A | 3/1983 |
| JP | 1993238705 A | 9/1993 |
| JP | 1993275406 A | 10/1993 |
| JP | 1993275407 A | 10/1993 |
| NL | 7807188 A | 1/1979 |
| WO | WO 8402650 A1 * | 7/1984 |
| WO | 9746283 A1 | 12/1997 |
| WO | 9929373 A1 | 6/1999 |
| WO | 2008083199 A | 7/2008 |
| WO | 2008089391 A1 | 7/2008 |
| WO | WO 2008083199 A1 * | 7/2008 |

OTHER PUBLICATIONS

Edwards et al., Tetrahedron Letters. vol. 31(4), pp. 3417-3420, 1990.*
Vander Meer et al., J. Econ.Entomol.78: 1190-1197 (1985).*
International Search Report and The Written Opinion of the International Searching Authority, PCT/US2011/029345, dated Mar. 22, 2011.
Reagen et al., Analytical Techniques and Method Validation for the Measurement of Selected Semivolatile and Nonvolatile Organofluorochemicals in Air', Journal of Occupational and Environmental Hygiene, taylor and Francis, Philadelphia, PA 2004, 559-569.
Benfodda et al., A convenient sysnthesis of N-functionalized perfluoroalkanesulfonamides, Phosphorus, sulfuf and Silicon and the related elements, Taylor and Francis, US, 185, 9, 2010, 1905-1914.
Honda et al., Molecular Aggregation Structure and Surface Properties of Polyfluoroalkyl acrylate Thin Films, Macromolecules, 2005, 38, 5699-5705, American Chemical Society.

* cited by examiner

*Primary Examiner* — Porfirio Nazario Gonzalez
*Assistant Examiner* — Kofi Adzamli

(57) ABSTRACT

The present invention relates to a polyfluoroalkylsulfonamido alkyl halide intermediate. The invention also relates to the use of the aforementioned halide intermediate to prepare a mixture of polyfluoroalkylsulfonamido alkyl amines including at least one polyfluoroalkylsulfonamido alkyl amine and its analog, a di(polyfluoroalkylsulfonamido alkyl) amine.

6 Claims, No Drawings

POLYFLUOROALKYLSULFONAMIDO ALKYL HALIDE INTERMEDIATE

FIELD OF THE INVENTION

The invention relates to a polyfluoroalkylsulfonamido alkyl halide intermediate. The invention also relates to the use of the polyfluoroalkylsulfonamido alkyl halide intermediate to prepare a mixture of polyfluoroalkylsulfonamido alkyl amines including at least one polyfluoroalkylsulfonamido alkyl amine and its analog, a di(polyfluoroalkylsulfonamido alkyl) amine.

BACKGROUND OF THE INVENTION

Polyfluoroalkylsulfonamido alkyl amines are useful starting materials for various products including: fluorinated surfactants, including cationic, non-ionic, anionic, and amphoteric surfactants, and fluorinated repellents, including poly(meth)acrylamides, ureas, imides. Specific applications for the products made from polyfluoroalkylsulfonamido alkyl amines include: electronics applications, nanotechnology, pharmaceutical and pesticide intermediates, catalysts, and firefighting foaming agents.

Conventional methods for making polyfluoroalkylsulfonamido alkyl amines typically provide low yields and produce an undesirable fluorine containing by-product which represents an economic loss. For example U.S. Pat. No. 4,486,391 contemplates making polyfluoroalkylsulfonamido alkyl amines by reacting a polyfluoroalkylsulfonic compound with a diamine as represented by the following:

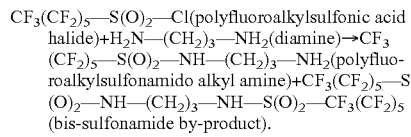

Like other conventional methods, U.S. Pat. No. 4,486,391 provides a synthetic route requiring a diamine reagent that, by definition, has two reactive amine sites per molecule, both of which can be converted to sulfonamido groups thereby forming a bis-sulfonamide by-product, which is also described in the GB patent 1,378,984. Conventional methods fail to disclose a synthetic route to a polyfluoroalkylsulfonamido alkyl amine that avoids the production of a bis-sulfonamide by-product, an undesirable impurity that typically worsens surfactancy, foaming properties, or other performance characteristics of desired products made from the polyfluoroalkylsulfonamido alkyl amine. Furthermore, the bis-sulfonamide by-product shares very similar physical properties with the desired polyfluoroalkylsulfonamido alkyl amine thus making its isolation and purification difficult and costly. In general, the bis-sulfonamide by-product constitutes a substantial loss of costly fluorinated starting material instead of the efficient incorporation of fluorine to make the desired polyfluoroalkylsulfonamido alkyl amine.

Because of the aforementioned disadvantages, it would be desirable to discover a method for making a polyfluoroalkylsulfonamido alkyl amine that avoids the use of a diamine reagent and the concomitant production of a bis-sulfonamide by-product.

BRIEF SUMMARY OF THE INVENTION

The present invention provides a method of making a polyfluoroalkylsulfonamido alkyl amine which avoids the use of a diamine reagent and the concomitant production of a bis-sulfonamide by-product. In addition to avoiding costly procedures to remove a bis-sulfonamide impurity, the present invention also avoids or drastically reduces the production of non-useful fluorine containing by-products. Contrary to conventional methods which use a diaminoalkane and polyfluoroalkylsulfonic compound, the present invention subjects a polyfluoroalkylsulfonamido alkyl halide to amino-de-halogenation with an amine thereby producing a polyfluoroalkylsulfonamido alkyl amine. Advantageously, the amino-de-halogenation also produces a di(polyfluoroalkylsulfonamido alkyl) amine, itself a useful product which can provide an advantage in lowering the surface tension and other performance characteristics of surfactants, made from the polyfluoroalkylsulfonamido alkyl amines. Therefore, contrary to conventional methods for making polyfluoroalkylsulfonamido alkyl amines that produce an undesirable non-useful by-product (e.g., bis-sulfonamide), the present invention produces a desirable useful co-product, which can be functionalized during the following surfactant synthesis, and therefore does not need to be removed. Accordingly, the present invention provides a method for making a mixture of polyfluoroalkylsulfonamido alkyl amines comprising at least one polyfluoroalkylsulfonamido alkyl amine and at least one di(polyfluoroalkylsulfonamido alkyl) amine.

In accordance with the invention, a mixture of polyfluoroalkylsulfonamido alkyl amines can be made by amino-de-halogenation wherein a polyfluoroalkylsulfonamido alkyl halide is reacted with ammonia or an amine, the polyfluoroalkylsulfonamido alkyl halide represented by

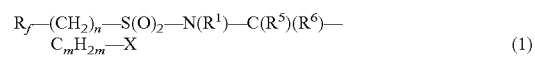

wherein:
$R_f$ is chosen from a $C_2$-$C_{12}$ polyfluoroalkyl optionally interrupted by one to four groups chosen from: —O—, —S—, —S(O)—, and —S(O)$_2$—;
n is chosen from an integer from 0 to 6; $R^1$, $R^5$, $R^6$ are independently chosen from hydrogen, $C_1$ to $C_6$ hydroxyalkyl, $C_1$ to $C_6$ halogen substituted alkyl, or a $C_1$ to $C_6$ linear or branched alkyl;
$C_mH_{2m}$ is linear or branched alkyl, and
m is chosen from an integer from 1 to 10; and
X is a halogen selected from Cl, Br, I, and mixtures thereof.

Preferred polyfluoroalkylsulfonamido alkyl halides of Formula 1 are those wherein;
$R_f$ is chosen from $CF_3(CF_2)_5$ or $CF_3(CF_2)_3$;
$R^1$, $R^5$, $R^6$ are independently chosen from hydrogen, methyl, or ethyl, $C_1$ to $C_3$ halogen substituted alkyl, $C_1$ to $C_3$ hydroxyalkyl, and most preferably hydrogen; n is chosen from 0 or 2;
m is 2; and
X is chlorine.

The ammonia or amine used during amino-de-halogenation of the polyfluoroalkylsulfonamido alkyl halide of Formula 1 to form the mixture of polyfluoroalkylsulfonamido alkyl amines is represented by:

wherein each $R^4$ is independently selected from hydrogen or a $C_1$ to $C_6$ alkyl, or a $C_1$ to $C_6$ hydroxyalkyl, preferably each $R^4$ is hydrogen thereby representing ammonia.

The polyfluoroalkylsulfonamido alkyl halides of Formula 1 can be made by reacting a polyfluoroalkylsulfonic compound with a monoamino alkyl halide, or salt thereof under suitable conditions to make a polyfluoroalkylsulfonamido alkyl halide wherein:
i) the polyfluoroalkylsulfonic compound is represented by

wherein $R_f$ and n are defined as above and Y is chosen from aryloxy, substituted aryloxy, or a halide such as F, Cl, or Br; and ii) the monoamino alkyl halide or salt thereof is represented by $$HN(R^1)\text{—}C(R^5)(R^6)\text{—}C_mH_{2m}\text{—}X \quad (4A)$$

or $$[H_2N(R^1)\text{—}C(R^5)(R^6)\text{—}C_mH_{2m}\text{—}X]^+X^- \quad (4B)$$

wherein $R^1$, $R^5$, $R^6$, and m are defined as above; and each X is a halogen independently chosen from Cl, Br, and I.

Alternatively, the polyfluoroalkylsulfonamido alkyl halides of Formula 1 can be made by reacting a polyfluoroalkylsulfonamido alkyl alcohol with a halogenating agent under suitable conditions to make a polyfluoroalkylsulfonamido alkyl halide wherein the polyfluoroalkylsulfonamido alkyl alcohol is represented by $$R_f\text{—}(CH_2)_n\text{—}S(O)_2\text{—}N(R^1)\text{—}C(R^5)(R^6)\text{—}C_mH_{2m}\text{—}OH \quad (5)$$

wherein $R_f$, n, $R^1$, $R^5$, $R^6$, and m are defined as above.

The polyfluoroalkylsulfonamido alkyl alcohols of Formula 5 can be made by reacting a polyfluoroalkylsulfonic compound of Formula 3 with an amino alkyl alcohol under suitable conditions to make a polyfluoroalkylsulfonamido alkyl alcohols wherein:

i) the amino alkyl alcohol is represented by $$HN(R^1)\text{—}C(R^5)(R^6)\text{—}C_mH_{2m}\text{—}OH \quad (6)$$

wherein $R^1$, $R^5$, $R^6$, and m are defined as above.

In accordance with the invention, the mixture of polyfluoroalkylsulfonamido alkyl amines comprises i) at least one polyfluoroalkylsulfonamido alkyl amine represented by $$R_f\text{—}(CH_2)_n\text{—}S(O)_2\text{—}N(R^1)\text{—}C(R^5)(R^6)\text{—}C_mH_{2m}\text{—}N(R^4)_2 \quad (7);$$

and ii) at least one di(polyfluoroalkylsulfonamido alkyl) analog of i) as represented by $$[R_f\text{—}(CH_2)_n\text{—}S(O)_2\text{—}N(R^1)\text{—}C(R^5)(R^6)\text{—}C_mH_{2m}\text{—}]_2N^{+k}(R^4)_{k+1}[Q^-]_k \quad (8);$$

wherein

Q is a monovalent anion preferebly chosen from halogen, alkylcarboxylate, alkylsulfonate, and more preferably halogen;

k is 0 or 1;

each $R_f$ is the same in i) and ii) and chosen from a $C_2$-$C_{12}$ polyfluoroalkyl optionally interrupted by one to four groups chosen from: —O—, —S—, —S(O)—, and —S(O)$_2$—;

each n in i) and ii) is the same and chosen from an integer from 0 to 6;

each m in i) and ii) is the same and chosen from an integer from 0 to 10;

each $R^1$, $R^5$, $R^6$ is independently chosen from hydrogen, $C_1$ to $C_6$ hydroxyalkyl, $C_1$ to $C_6$ halogen substituted alkyl, or a $C_1$ to $C_6$ linear or branched alkyl; provided that each $R^1$ in i) and ii) are the same, each $R^5$ in i) and ii) are the same, and each $R^6$ in i) and ii) are the same;

each $R^4$ in i) and ii) are the same and chosen from hydrogen or a $C_1$ to $C_6$ alkyl, preferably hydrogen.

DETAILED DESCRIPTION OF THE INVENTION

The various reactions resulting in the formation of the desired polyfluoroalkylsulfonamido alkyl amine mixture (Formulae 7 & 8) of the invention may be represented as follows:

Reaction 1: Formation of the mixture of polyfluoroalkylsulfonamido alkyl amines of Formulae 7 and 8

$$R_f\text{—}(CH_2)_n\text{—}S(O)_2\text{—}N(R^1)\text{—}C(R^5)(R^6)\text{—}C_mH_{2m}\text{—}X\text{(Formula 1: polyfluoroalkylsulfonamido alkyl halide)}+N(R^4)_2H\text{(Formula 2:ammonia or amine)}\rightarrow R_f\text{—}(CH_2)_n\text{—}S(O)_2\text{—}N(R^1)\text{—}C(R^5)(R^6)\text{—}C_mH_{2m}\text{—}N(R^4)_2+[R_f\text{—}(CH_2)_n\text{—}S(O)_2\text{—}N(R^1)\text{—}C(R^5)(R^6)\text{—}C_mH_{2m}\text{—}]_2N^{+k}(R^4)_{k+1}[Q^-]_k$$

Reaction 2: Formation of polyfluoroalkylsulfonamido alkyl halide of Formula 1

$$R_f\text{—}(CH_2)_n\text{—}S(O)_2\text{—}Y\text{(polyfluoroalkylsulfonic compound of Formula 3)}+H_2N(R^1)\text{—}C(R^5)(R^6)\text{—}C_mH_{2m}\text{—}X \text{ or } [H_2N(R^1)\text{—}C(R^5)(R^6)\text{—}C_mH_{2m}\text{—}X]^+X^-\text{(Formula 4A or 4B: monoamino alkyl halide or salt thereof)}\rightarrow R_f\text{—}(CH_2)_n\text{—}S(O)_2\text{—}N(R^1)\text{—}C(R^5)(R^6)\text{—}C_mH_{2m}\text{—}X$$

Reaction 3: Formation of polyfluoroalkylsulfonamido alkyl halide of Formula 1 by halo-de-hydroxylation of alcohols of Formula 5

$$R_f\text{—}(CH_2)_n\text{—}S(O)_2\text{—}N(R^1)\text{—}C(R^5)(R^6)\text{—}C_mH_{2m}\text{—}OH\text{(Formula 5:polyfluoroalkylsulfonamido alkyl alcohol)}+\text{halogenating agent}\rightarrow R_f\text{—}(CH_2)_n\text{—}S(O)_2\text{—}N(R^1)\text{—}C(R^5)(R^6)\text{—}C_mH_{2m}\text{—}X$$

Reaction 4: Formation of polyfluoroalkylsulfonamido alkyl alcohol of Formula 5

$$R_f\text{—}(CH_2)_n\text{—}S(O)_2\text{—}Y\text{(Formula 3:polyfluoroalkylsulfonic compound)}+HN(R^1)\text{—}C(R^5)(R^6)\text{—}C_mH_{2m}\text{—}OH\text{(Formula 6:amino alkyl alcohol)}\rightarrow R_f\text{—}(CH_2)_n\text{—}S(O)_2\text{—}N(R^1)\text{—}C(R^5)(R^6)\text{—}C_mH_{2m}\text{—}OH+HM$$

In preferred conditions of the Reaction 1, polyfluoroalkylsulfonamido alkyl halide of Formula 1 undergoes amino-de-halogenation with ammonia, producing polyfluoroalkylsulfonamido alkyl amine of Formula 7, which upon further amino-de-halogenation reaction with alkyl halide of Formula 1 produces di(polyfluoroalkylsulfonamido alkyl) amine of Formula 8. Therefore, polyfluoroalkylsulfonamido alkyl amines of Formulae 7 and 8 are both present in the product mixture. An example of the reaction conditions for subjecting a polyfluoroalkylsulfonamido alkyl halide (Formula 1) to amino-de-halogenation thereby producing a mixture of polyfluoroalkylsulfonamido alkyl amines (Formulae 7 and 8) includes charging a reaction vessel with a polyfluoroalkylsulfonamido alkyl halide, and optionally an iodide salt catalyst, and solvent, which is then sealed, evacuated, and then charged with concentrated ammonia solution in water or methanol, preferably anhydrous ammonia, and heated to a reaction temperature of about 100 to 130° C., more preferably between 110 and 120° C. in a pressurized reactor. The pressure of the reactor is primarily determined by the partial pressure of ammonia at the reaction temperature and is about 70 to 600 psi. To maintain a high ratio (from about 10:1 to about 99:1) of amine of Formula 7 to amine of Formula 8, a 10 to 200 fold molar excess of ammonia to polyfluoroalkylsulfonamido alkyl halide may be used; preferably a 25 to 150 molar excess, and more preferably a 30 to 100 molar excess. The reaction temperature is maintained for about 4 to 12 hours. The contents of the reactor are then cooled to about 20 to 25° C., and excess of ammonia is vented out. The unused ammonia can be scrubbed or condensed to recycle into the next reaction batch. The contents of the reactor are optionally filtered. A strong base (e.g., NaOH, KOH), preferably in powdered form, to convert the ammonium salts to a corresponding amines, and, optionally, activated carbon, to reduce the color of the mixture or final product, can then be added to the mixture of product, solvent and ammonium salts, allowed to stir, and filtered, to obtain the solution of the product. The solvent can then be evaporated from the filtrate with vacuum to obtain a solid product comprising typically 70 to 98 wt. % of a mixture of polyfluoroalkylsulfonamido alkyl amines (Formulae 7 and 8).

Suitable solvents for conducting the amino-de-halogenation of Reaction 1 include polar solvents such as ethers, e.g., 1,2-dimethoxyethane, or alkyl alcohols. Alkyl alcohols (e.g., methanol, ethanol, 2-propanol, and 1-butanol) are preferred for their ability to dissolve the product of Reaction 1 and the reactants thereof.

Suitable amino-de-halogenation catalysts for use in Reaction 1 include iodide salts such as NaI, KI, Bu$_4$NI. These iodide salts are used preferably at 0.1 to 1.5 molar equivalents based on the starting compound of Formula 1, and more preferably at 0.1 to 0.3 molar equivalents. When polyfluoroalkylsulfonamido alkyl iodides are used for the Reaction 1, the use of additional iodide salts is not necessary.

While concentrated ammonia is preferred, with anhydrous ammonia most preferred to react with the polyfluoroalkylsulfonamido alkyl halide in Reaction 1, alkyl amines (represented by Formula 2), with optional addition of other bases, may be used instead of ammonia. Examples of such amines include methylamine, ethylamine, butylamine, hexylamine, 2-aminoethanol, 2-(methylamino)-1-ethanol.

Referring to Reaction 2, an example of the reaction conditions for forming a polyfluoroalkylsulfonamido alkyl halide of Formula 1 includes dissolving a monoamino alkyl halide or salt thereof (Formulae 4A or 4B) in a vessel (preferably under inert anhydrous conditions, e.g., with nitrogen purge) containing an appropriate aprotic solvent and additional base. The vessel is equipped with mechanical stirrer and a condenser. The contents of the vessel are heated to a temperature of about 10-20° C.; after which, a polyfluoroalkylsulfonic compound (Formula 3) is added to the vessel over a period of about 15 to 120 minutes while maintaining the temperature between about 10 to 50° C., more preferably between 20 and 40° C. The temperature can be controlled by means of the addition rate and external cooling. After addition of the polyfluoroalkylsulfonic compound, a reaction temperature is maintained at about 25 to 65° C. depending upon what additional base is used. After about 98 to 100 wt. % consumption of the polyfluoroalkylsulfonic acid halide (as measured by gas chromatography (GC) analysis), a strong acid (e.g., HCl or H$_3$PO$_4$) may be added to adjust the pH to about 2 to 7 (preferably 4 to 5) causing the conversion of unreacted monoamino alkyl halide to a corresponding ammonium alkyl halide salts of Formula 4B, and conversion of additional base to its corresponding salts of these strong acids, which are removed by filtration. The filtrate can be further dried in vacuum to remove solvent and obtain solid product. Product or its solution in appropriate solvent can be optionally washed with water to remove traces of salts.

Examples of the aforementioned additional base include tertiary amines, e.g., triethylamine, diisopropyl ethyl amine, N,N,N',N'-tetramethyl ethylene diamine, a hindered tertiary amine such as diaza(1,3)bicyclo[5,4,0]undecane (DBU), pyridine, and weak inorganic bases such as potassium carbonate. Depending upon the choice of base, the reaction temperature can vary. When a tertiary amine base is used, the typical reaction temperature is about 10 to 40° C. When the potassium carbonate is used, a higher reaction temperature, about 50 to 65° C., is preferred to increase the rate of the reaction.

When conducting the Reaction 2 of polyfluoroalkylsulfonic compound with monoamino alkyl halides (Formula 4A) without additional base, the molar ratio of the monoamino alkyl halide with respect to the polyfluoroalkylsulfonic compound is preferably between 2.5:1 and 2:1, and more preferably between 2.2:1 and 2:1. The excess beyond the first molar equivalent of the monoamino alkyl halide of Formula 4A is intended as a base to neutralize the generated HY acid, where Y is defined above. If an monoamino alkyl halide or salt thereof and an additional base is used, then the molar ratio of monoamino alkyl halide or salt thereof to the polyfluoroalkylsulfonic compound can be reduced below 2:1 down to about 1:1, and more preferably between 1.4:1 and 1:1.

Examples of suitable monoamino alkyl halides (Formula 4A) for use in the amination of Reaction 2 include 2-chloro-1-ethaneamine, 2-bromo-1-ethanamine, 3-chloro-1-propanamine, 3-bromo-1-propanamine, 3-chloro-N-methyl-1-propanamine, 3-bromo-N-methyl-1-propanamine, 3-chloro-N-(3-chloropropyl)-1-propanamine, 2-chloro-N-(2-chloroethyl)-1-ethanamine, 4-chloro-1-butanamine, 4-bromo-1-butanamine, 4-chloro-2-butanamine, 4-chloro-N-methyl-1-butanamine, 4-bromo-N-methyl-1-butanamine, 5-chloro-1-pentanamine, 5-chloro-N-methyl-1-pentanamine, 5-bromo-1-pentanamine, 5-bromo-N-methyl-1-pentanamine, and their isomers.

Examples of suitable monoamino alkyl halide salts (Formula 4B) for use in the amination of Reaction 2 include 2-chloro-1-ethaneaminehydrochloride, 3-chloro-1-propanamine hydrochloride, N-(2-chloroethyl)-2-amino-1-chloroethane hydrochloride. Monoamino alkyl halide salts are more readily commercially available and are thus preferred over their monoamino alkyl halide counterparts.

Suitable solvents for conducting the Reaction 2 are commercially available and include methylene chloride, butyronitrile, 1,2-dimethoxyethane, 1,2-diethoxyethane, diethyl ether, tetrahydrofuran, ethyl acetate, toluene, and mixtures thereof.

Referring to Reaction 3, an example of the reaction conditions for forming a polyfluoroalkylsulfonamido alkyl halide (Formula 1) by halo-de-hydroxylation of a polyfluoroalkylsulfonamido alkyl alcohol of (Formula 5) includes: charging a stirred vessel with polyfluoroalkylsulfonamido alkyl alcohol dissolved in an aprotic solvent; the addition of a halogenation agent; reacting the contents of the vessel at a temperatures determined by the reactivity of the halogenating agent, typically between about 40 to 130° C., for about 30 to 240 minutes; and removing solvent and excess halogenation agent by distillation, and, optionally, hydrolysis, and further aqueous washing, to obtain crude product. The crude product can be further purified by recrystallization, e.g., from hydrocarbon solvent such as hexane or heptane.

Examples of halogenation agents for use in Reaction 3 include various chlorinating or brominating agents, such as: acid halides, e.g., thionyl chloride, thionyl bromide, oxalyl chloride, or hydrogen chloride; as well as other reagents that enable the exchange of —OH for —Cl, such as PPh$_3$/Cl$_3$CCONH$_2$. Preferably, the halogenation agent is thionyl chloride used in an amount suitable to achieve substantially complete conversion of the polyfluoroalkylsulfonamido alkyl alcohol while avoiding significant excess of thionyl chloride. Examples of suitable molar equivalents of thionyl chloride to polyfluoroalkylsulfonamido alkyl alcohol include about 1 to 5 molar equivalents, with about 1.5 molar equivalents being preferable. Typical reaction with thionyl chloride involves controlling its addition and maintaining the reaction temperature at about 20 to 60° C. Higher reaction temperatures for thionyl chloride are possible, but have been found to generate a greater proportion of undesirable and dark-colored by-products.

Examples of suitable aprotic solvents for use in the halogenation of Reaction 3 include methylene chloride, butyronitrile, 1,2-dimethoxyethane, 1,2-diethoxyethane, diethyl ether, tetrahydrofuran, ethyl acetate, toluene, and mixtures thereof.

Referring to Reaction 4, an example of the reaction conditions for forming a polyfluoroalkylsulfonamido alkyl alcohol of Formula 5 includes dissolving a amino alkyl alcohol (Formula 6) preferably 2 to 2.3 equivalents based on the polyfluoroalkylsulfonic compound of Formula 3, in a vessel (preferably under inert anhydrous conditions, e.g., with nitrogen purge) containing an appropriate solvent. The vessel is equipped with mechanical stirrer and a condenser. The contents of the vessel are maintained at a temperature of about 10-20° C.; after which, a polyfluoroalkylsulfonic compound (Formula 3) is added to the vessel over a period of about 15 to 120 minutes while maintaining the temperature between about 10-50° C., more preferably between 20 and 40° C. The temperature can be controlled by means of the addition rate and external cooling. After addition of the polyfluoroalkylsulfonic compound, the reaction is maintained at a temperature of about 25 to 55° C. After about 99 to 100 wt. % consumption of the polyfluoroalkylsulfonic compound (as measured by gas chromatography (GC) analysis), a strong acid (e.g., HCl or $H_3PO_4$) is added to adjust the pH to about 2 to 7 (preferably 4 to 5) causing the neutralization of unreacted aminoalkylalcohol of Formula 6, to form additional amount of ammonium halide salts of aminoalkylalcohol by-products which have lower solubility in the reaction solvent and are removed by filtration. The filtrate solution can be further dried in vacuum to remove solvent and obtain solid product. Product or its solution in appropriate solvent can be optionally washed with water to remove traces of salts.

Examples of suitable solvents for use in Reaction 4 are commercially available and include aprotic solvents, such as methylene chloride, butyronitrile, 1,2-dimethoxyethane, 1,2-diethoxyethane, diethyl ether, tetrahydrofuran, ethyl acetate, toluene, as well as tertiary alcohols (e.g., t-butanol and t-amyl alcohol), and mixtures thereof.

When conducting Reaction 4, the molar ratio of the amino alkyl alcohol to the polyfluoroalkylsulfonic compound is preferably at least 2:1, more preferably between 2.5:1 and 2.0:1, and still more preferably between 2.2:1 and 2:1. The excess beyond the first molar equivalent of the polyfluoroalkylsulfonamido alkyl alcohol is intended as a base to neutralize generated acid represented in Reaction 4 as HM. If an additional base is used, then the molar ratio of amino alkyl alcohol (Formula 6) to the polyfluoroalkylsulfonic compound (Formula 3) can be reduced below 2:1 down to about 1:1.

Examples of suitable amino alkyl alcohols (Formula 6) for use in Reaction 4 are commercially available and include 2-(methylamino)ethanol, 3-amino-1-propanol, ethanolamine, diethanolamine, 3-(3-hydroxypropyl-amino)-propan-1-ol, 4-amino butan-1-ol, 1-amino-2-propanol, 2-amino-1-propanol, 3-(methylamino)-1-propanol, 3-amino-2-methyl-1-Propanol, 4-amino-1-butanol, 3-amino-1-butanol, 2-amino-3-methyl-1-butanol, 4-amino-2-methyl-1-butanol, 4-(methylamino)-1-butanol, 5-amino-1-pentanol, 5-(ethylamino)-1-pentanol, leucinol, isoleucinol, 6-amino-1-hexanol, 5-amino-2,2-dimethylpentanol, and their isomers.

EXAMPLES

Reaction 1

Examples 1-7 show how embodiments of Reaction 1 were conducted.

Example 1

$CF_3(CF_2)_5C_2H_4SO_2NH(CH_2)_3Cl+NH_3+Kl$ 2-propanol→$CF_3(CF_2)_5C_2H_4SO_2NH(CH_2)_3NH_2$ 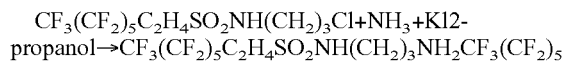
$C_2H_4SO_2NH(CH_2)_3Cl$ (10 g, 0.02 mol), 2-propanol (30 g), potassium iodide (Kl, 0.33 g, 0.002 mol) were charged to the 210 mL HASTELLOY-C shaker tube. The shaker tube was sealed, evacuated, and charged with $NH_3$ (gas, anhydrous, 29 g, 1.7 mol) and heated at 110° C. for 8 hours at 720 psi. The excess of $NH_3$ was vented. The product mixture was filtered at 60° C. The product filtrate was treated with solid NaOH powder, activated carbon and filtered. The solvent was evaporated in vacuum to obtain orange to brown solid containing $CF_3(CF_2)_5C_2H_4SO_2NH(CH_2)_3NH_2$ (80 wt %), $CF_3(CF_2)_5C_2H_4SO_2NH_2$ (13 wt %), and $(CF_3(CF_2)_5C_2H_4SO_2NH(CH_2)_3)_2NH$ (2-3 wt %) as determined by GC and $^{13}C$ NMR analyses. $C_6F_{13}C_2H_4SO_2NHC_3H_6NH_2$: $^1H$ NMR (DMSO-$d_6$) δ 1.75 (p, 2H, $CH_2CH_2CH_2$, J=7 Hz), 2.59 (m, 2H), 2.81 (t, 2H, J=7.7 Hz), 3.05 (t, 2H, J=7.0 Hz), 3.44 (m, 2H). $^{13}C$ NMR (DMSO-$d_6$) δ 120-105 (m, 6C), 42.84 (1C), 39.73 (1C), 37.13 (1C), 29.45 (1C), 25.52 (t, 1C, $CH_2CF_2$, J=22.8 Hz).

Example 2

$CF_3(CF_2)_5C_2H_4SO_2NH(CH_2)_3Cl+NH_3+Kl$, 1,2-dimethoxyethane→$CF_3(CF_2)_5C_2H_4SO_2NH(CH_2)_3NH_2$ $CF_3(CF_2)_5C_2H_4SO_2NH(CH_2)_3Cl$ (25 g, 0.05 mol), 1,2-dimethoxyethane (87 g), potassium iodide (Kl, 0.82 g, 0.005 mol) were charged to the 400 mL HASTELLOY-C shaker tube. The shaker tube was sealed, evacuated, and charged with $NH_3$ (gas, anhydrous, 13.6 g, 0.8 mol) and heated at 120° C. for 4 hours at 355 psi. The reaction mixture was cooled and the excess of $NH_3$ was vented. The product mixture was treated with solid NaOH powder and additional 2-propanol at 60° C. and filtered. The solvent from the filtrate was evaporated in vacuum to obtain yellow solid containing $CF_3(CF_2)_5C_2H_4SO_2NH(CH_2)_3NH_2$ (56 wt. %), $CF_3(CF_2)_5C_2H_4SO_2NH_2$ (16 wt. %), and $(CF_3(CF_2)_5C_2H_4SO_2NH(CH_2)_3)_2NH$ (24 wt. %) as determined by GC and $^{13}C$ NMR analyses.

Example 3

$C_6F_{13}C_2H_4SO_2NH(CH_2)_3Cl+NH_3+Kl$, 1-Butanol→$C_6F_{13}C_2H_4SO_2NH(CH_2)_3NH_2$ $C_6F_{13}C_2H_4SO_2NH(CH_2)_3Cl$ (10 g, 0.02 mol), 1-butanol (130 g), potassium iodide (Kl, 0.5 g, 0.003 mol) were charged to the 210 mL HASTELLOY-C shaker tube. The shaker tube was sealed, evacuated, charged with $NH_3$ (gas, anhydrous, 2.0 g, 0.12 mol) and heated at 120° C. for 5 hours at pressure of 70-85 psi. The reaction mixture was cooled and the excess of $NH_3$ was vented. The product solution in BuOH was heated to 60° C., filtered and washed with 2.5% NaOH aqueous solution. The solvent from was evaporated in vacuum to obtain brown solid (9.4 g) containing $C_6F_{13}C_2H_4SO_2NH(CH_2)_3NH_2$ (48 wt. %), $C_6F_{13}C_2H_4SO_2NH_2$ (13 wt. %), and $(C_6F_{13}C_2H_4SO_2NHO_3H_6)_2NH$ (39 wt. %) based on $^{13}C$ NMR analysis. $(C_6F_{13}C_2H_4SO_2NHO_3H_6)_2NH$: $^1H$ NMR (EtOH-$d_6$) δ 1.76 (m, 4H), 2.69 (m, 8H), 3.17 (m, 4H), 3.30 (m, 4H), 5.19 (broad). $^{13}C$ NMR (MeOH-$d_4$) δ 120-105 (m, 12C), 48.64 (2C), 44.54 (2C), 42.66 (2C), 32.96 (2C), 28.50 (t, 2C, $CH_2CF_2$, J=21 Hz).

Example 4

$C_6F_{13}C_2H_4SO_2NH(CH_2)_3Cl+C_6F_{13}C_2H_4SO_2NH(CH_2)_3NH_2$→$(C_6F_{13}C_2H_4SO_2NHO_3H_6)_2NH$
$C_6F_{13}C_2H_4SO_2NH(CH_2)_3Cl$ (0.6 g, 1.2 mmol), $C_6F_{13}C_2H_4SO_2NH(CH_2)_3NH_2$ (0.58 g, 1.2 mmol), 1-butanol (9 g), NaOH (0.19 g of 35% aqueous solution) and NaI (0.09 g, 0.6 mmol) were placed in the 50 mL flask with magnetic stirring. The reaction mixture was heated at 100° C. for 14 hours. The GC analysis indicated 67% conversion of starting $C_6F_{13}C_2H_4SO_2NH(CH_2)_3NH_2$. The reaction mixture was cooled to 50° C., and the mixture was washed with water (5 g). The product was crystallized from butanol/toluene to obtain 0.2 g of yellow solid containing mostly $(C_6F_{13}C_2H_4SO_2NHC_3H_6)_2NH$ (71 wt %) and $C_6F_{13}C_2H_4SO_2NHC_3H_6NH_2$ (29 wt %) by $^{13}C$ NMR. After the drying of the filtrate solution additional 0.9 g of yellow solid was obtained, containing approximately $C_6F_{13}C_2H_4SO_2NH_2$ (14 wt %), 1-[(2-perfluorohexylethyl)sulfonyl]-azetidine (49 wt %), and $C_6F_{13}C_2H_4SO_2NHO_3H_6NH_2$ (31 wt %), by GC analysis. 1-[(2-perfluorohexylethyl)sulfonyl]-azetidine: GC/MS (m/z): 43 (30), 56 (100), 57 (72), 65 (28), 69 (42), 77 (32), 104 (21), 120 (23), 131 (20), 148 (35), 169 (8), 213 (11), 263 (12), 277 (23), 327 (54), 356 (5), 384 (6), 420 (5), 448 (6), 467 (6, M+). $^1H$ NMR (CDCl$_3$) δ 2.28 (p, 2H, CH$_2$CH$_2$CH$_2$, J=7.6 Hz), 2.59 (m, 2H, CH$_2$CF$_2$), 3.13 (m, 2H, CH$_2$SO$_2$), 4.00 (t, 4H, CH$_2$N, J=7.6 Hz). $^{13}C$ NMR (CDCl$_3$) δ 121-105 (m, 6C), 50.52 (2C), 42.54 (t, 1C, CH$_2$CH$_2$CF$_2$, J=4.5 Hz), 26.21 (t, 1C, CH$_2$CF$_2$, J=22.9 Hz), 15.09 (1C).

Example 5

Preparation of $CF_3(CF_2)_5CH_2CH_2SO_2NH(CH_2)_3NH(CH_2)_2OH$ from $CF_3(CF_2)_5CH_2CH_2SO_2NH(CH_2)_3Cl$ and $NH_2(CH_2)_2OH$ $CF_3(CF_2)_5(CH_2)_2SO_2NH(CH_2)_3Cl$ (3.8 g, 0.008 mol), amino ethanol (1.3 g, 0.021 mol), 1-butanol (14 g), and NaI (0.3 g, 0.002 mol) were placed in the 50 mL flask with magnetic stirring. The reaction mixture was heated at 100° C. for 18 hours. The GC analysis indicated complete conversion of $CF_3(CF_2)_5(CH_2)_2SO_2NH(CH_2)_3Cl$. The reaction mixture was cooled to 50° C., and the excess of base was neutralized with 0.57 g of 35% HCl and washed with water (12 g). The butanol solution was dried on rotary evaporator to obtain 3.8 g of product (87% purity by GC, 83% yield). $^1H$ NMR (DMSO-d$_6$) δ 1.74 (p, 2H, CH$_2$CH$_2$CH$_2$, J=7 Hz), 2.61 (m, 2H, CH$_2$CF$_2$), 2.74 (m, 4H), 3.10 (t, 2H, J=7 Hz), 3.31 (m, 2H), 3.58 (t, 2H, J=5.5 Hz), 5.32 (broad). $^{13}C$ NMR (DMSO-d$_6$) δ 120-105 (m, 60), 56.34 (1C), 49.10 (1C), 44.47 (1C), 42.13 (1C), 39.85 (1C), 26.24 (1C), 25.52 (t, 1C, CH$_2$CF$_2$, J=21.8 Hz).

Example 6

Preparation of $CF_3(CF_2)_5CH_2CH_2SO_2NH(CH_2)_3N(CH_3)(CH_2)_2OH$ from $CF_3(CF_2)_5CH_2CH_2SO_2NH(CH_2)_3Cl$ and $NH(CH_3)(CH_2)_2OH$ $CF_3(CF_2)_5(CH_2)_2SO_2NH(CH_2)_3Cl$ (2.9 g, 0.006 mol), 2-(N-methylamino)ethanol (1.4 g, 0.019 mol), 1-butanol (11 g), and NaI (0.22 g, 0.001 mol) were placed in the 50 mL flask with magnetic stirring. The reaction mixture was heated at 100° C. for 10 hours. The GC analysis indicated complete conversion of $CF_3(CF_2)_5(CH_2)_2SO_2NH(CH_2)_3Cl$. The reaction mixture was washed with water at 50° C. (2×9 g). The butanol solution was dried to obtain 2.67 g of product (93% purity by GC, 80% yield). $^1H$ NMR (CDCl$_3$) δ 1.62 (p, 2H, CH$_2$CH$_2$CH$_2$, J=6.8 Hz), 2.18 (s, 3H, NCH$_3$), 2.40 (m, 4H), 2.64 (m, 2H, CH$_2$CF$_2$), 3.01 (t, 2H, CH$_2$N, J=6.8 Hz), 3.28 (m, 2H, CH$_2$SO$_2$), 3.48 (t, 2H, CH$_2$N, J=6.3 Hz), 4.5 (broad), 7.5 (broad). $^{13}C$ NMR (DMSO-d$_6$) δ 125-105 (m, 6C), 59.29 (1C), 58.70 (1C), 54.71 (1C), 42.03 (2C), 40.76 (1C), 27.01 (1C), 25.62 (t, 1C, CH$_2$CF$_2$, J=22.4 Hz).

Example 7

Preparation of $C_6F_{13}CH_2CH_2SO_2NHC_3H_6NH(CH_2)_6H$ from $C_6F_{13}CH_2CH_2SO_2NHC_3H_6Cl$ and $NH_2(CH_2)_6H$ $C_6F_{13}CH_2CH_2SO_2NH(CH_2)_3Cl$ (2.5 g, 4.7 mmol), hexylamine (1.5 g, 15 mmol), 1-butanol (10 g), and NaI (0.21 g, 1.4 mmol) were placed in the 50 mL flask with magnetic stirring. The reaction mixture was heated at 100° C. for 10 hours. The GC analysis indicated complete conversion of $C_6F_{13}CH_2CH_2SO_2NH(CH_2)_3Cl$. The reaction mixture was cooled to 50° C., and the excess of base was neutralized with 0.59 g of 35% HCl and butanol solution washed with water (2×8 g). The solution was cooled, and the product was crystallized, filtered out and dried to obtain 1.3 g of yellow powder solid (93.8% purity by GC). The filtrate was evaporated to obtain additional 1.27 g of waxy solid containing additional product (30% by GC). Combined yield 63%.

$C_6F_{13}CH_2CH_2SO_2NHC_3H_6NH(CH_2)_6H$: $^1H$ NMR (MeOH-d$_4$) δ 0.92 (t, 3H, CH$_3$, J=6 Hz), 1.35 (m, 6H), 1.69 (p, 2H, CH$_2$, J=7 Hz), 1.94 (p, 2H, CH$_2$, J=7 Hz), 2.67 (m, 2H, CH$_2$CF$_2$), 3.00 (t, 2H, J=7.9 Hz), 3.10 (t, 2H, J=7.9 Hz), 3.22 (t, 2H, J=6.6 Hz), 3.36 (m, 2H, CH$_2$SO$_2$), 4.78 (broad). $^{13}C$ NMR (MeOH-d$_4$) δ 120-105 (m, 6C), 49.18 (1C), 46,36 (1C), 44.27 (1C), 40.90 (1C), 32.38 (1C), 28.33 (1C), 27.24 (m, 3C), 23.43 (1C), 14.23 (1C).

Reaction 2 with Monoamino Alkyl Halide Salt

Examples 8-10 show how embodiments of Reaction 2 were conducted wherein a polyfluoroalkylsulfonamido alkyl halide, $CF_3(CF_2)_5(CH_2)_2SO_2NH(CH_2)_3Cl$, was formed by reacting a polyfluoroalkylsulfonic compound, $CF_3(CF_2)_5(CH_2)_2SO_2Cl$, with a monoamino alkyl halide salt, [H$_3$N(CH$_2$)$_3$Cl]$^+$Cl$^-$ (3-chloropropylamine hydrochloride) Example 8 used Et$_3$N (triethylamine) as an added base. Example 9 used K$_2$CO$_3$ as an added base. Example 10 used DBU (diaza(1,3)bicyclo[5.4.0]-undecane) as an added base.

Example 8

$CF_3(CF_2)_5(CH_2)_2SO_2Cl$ (10 g), 3-chloropropyl amine hydrochloride (4.1 g), and 1,2-dimethoxyethane (20 g) solvent were added to the round bottom flask equipped with mechanical stirring under nitrogen. Solution of triethylamine (4.5 g) in 1,2-dimethoxyethane (10 g) solvent was added dropwise during 30 min at 20-30° C. at 250 rpm. Stirred for 12 h after the addition is completed. The reaction was monitored by GC to ensure the complete conversion 1. The final reaction mixture with pH of about 5 was filtered from solids through 2 mm layer of CELITE 545. The solids were washed with 1,2-dimethoxyethane (7 g) and combined filtrate was evaporated in vacuum to obtain 11.0 g of $CF_3(CF_2)_5(CH_2)_2SO_2NH(CH_2)_3Cl$. The product was additionally dissolved in hot toluene (8 g) and washed with 15.5 mL of 1 wt % HCl aqueous solution to remove traces of $NH_2(CH_2)_3Cl$.

Example 9

3-chloropropyl amine hydrochloride (4.7 g), K$_2$CO$_3$ (6.9 g) and 1,2-dimethoxyethane (19.3 g) solvent were placed in the round bottom flask equipped with mechanical stirring under nitrogen. Solution of 2-(perfluorohexyl)ethanesulfonyl chloride $CF_3(CF_2)_5(CH_2)_2SO_2Cl$ (10.1 g), in 1,2-dimethoxyethane (10 g) solvent was added dropwise during 1 hour at room temperature while stirring at 250 rpm. After the addition was completed, the reaction was gradually heated to 75° C. and reacted for 12 h. The reaction was monitored by GC to ensure the complete conversion of $CF_3(CF_2)_5(CH_2)_2SO_2Cl$. The final reaction mixture with pH=3.5 was cooled down and filtered from solids through 2 mm layer of CELITE 545. The solids were washed with 1,2-dimethoxyethane (10 mL) and combined filtrate was evaporated in vacuum to obtain 8.2 g of $CF_3(CF_2)_5(CH_2)_2SO_2NH(CH_2)_3Cl$. The product was additionally dissolved in hot toluene (8 g) and washed with 15.5 mL of 1 wt % HCl aqueous solution.

Example 10

3-chloropropylamine hydrochloride (6.0 g), diaza(1,3)bicyclo[5.4.0]-undecane (DBU, 4.1 g) and 1,2-dimethoxyethane (21.5 g) solvent were placed in the round bottom flask equipped with mechanical stirring under nitrogen. Solution of 2-(perfluorohexyl)ethanesulfonyl chloride $CF_3(CF_2)_5(CH_2)_2SO_2Cl$ (10.1 g), in 1,2-dimethoxyethane (10 g) solvent was added dropwise during 30 minutes at 20-25° C. while stirring at 250 rpm. Then additional DBU (2.6 g) was added. Reaction mixture was stirred for 2 h after the DBU addition was completed. The reaction was monitored by GC to ensure the complete conversion of 2-(perfluorohexyl)ethanesulfonyl chloride. The final reaction mixture was filtered from solids through 2 mm layer of CELITE 545. The solids were washed with 1,2-dimethoxyethane and combined filtrate was evaporated in vacuum to obtain 11.3 g of crude $CF_3(CF_2)_5(CH_2)_2SO_2NH(CH_2)_3Cl$ as yellow solid. 9.5 g of the crude product was additionally dissolved in hot toluene (7 g) and washed with 14 mL of 2.5 wt % HCl aqueous solution, followed with 12 mL water wash. Toluene solution was evaporated in vacuum to obtain 8.35 g of $CF_3(CF_2)_5(CH_2)_2SO_2NH(CH_2)_3Cl$ (GC purity 93%, yield 88%).

Reaction 3

Examples 11-15 show how embodiments of Reaction 3 were conducted.

Example 11

Preparation of $CF_3(CF_2)_5(CH_2)_2SO_2NH(CH_2)_3Cl$ from $CF_3(CF_2)_5(CH_2)_2SO_2NH(CH_2)_3OH$ using thionyl chloride.

$CF_3(CF_2)_5CH_2CH_2SO_2NH(CH_2)_3OH$ (15 g, 31 mmol.) product of the Example 16 and 30 mL of 1,2-dimethoxyethane was heated to 40° C. to dissolve. Thionyl chloride ($SOCl_2$, 5.47 g, 46 mmol.) was added dropwise to this solution during 30 min, and the resulting mixture was stirred at 40° C. for another 30 min. $K_2CO_3$ (2.35 g) was added and stirred at 40° C. for 30 min. The solution was decanted and solvent removed on rotary evaporator to obtain 13 g of white solid product. GC/MS (m/z): 56 (3), 69 (6), 77 (6), 119 (4), 131 (4), 140 (5), 169 (4), 213 (2), 263 (4), 277 (3), 327 (6), 376 (8), 420 (2), 440 (100), 441 (10), 484 (2), 486 (1), 504 (0.5). $^1$H NMR (CDCl$_3$) δ 2.03 (p, 2H, CH$_2$CH$_2$CH$_2$, J=6.4 Hz), 2.60 (tm, 2H, CH$_2$CF$_2$, J=17.5 Hz), 3.26 (m, 2H, CH$_2$SO$_2$), 3.32 (t, 2H, CH$_2$N, J=6.5 Hz), 3.62 (t, 2H, CH$_2$Cl, J=6.0 Hz), 4.88 (1H, broad s). $^{13}$C NMR (CDCl$_3$) δ 125-105 (m, 6C), 43.15 (b, 1C), 41.38 (1C), 39.68 (1C), 32.45 (1C), 26.00 (t, 1C, CH$_2$CF$_2$, J=22.8 Hz).

Example 12

Preparation of $CF_3(CF_2)_5(CH_2)_2SO_2NH(CH_2)_3Cl$ using hydrogen chloride $CF_3(CF_2)_5CH_2CH_2SO_2NH(CH_2)_3OH$ (7 g, 0.014 mol, MW=485), 1,2-dimethoxyethane (10 g) and pyridine (0.7 g, 0.009 mol) were charged to the 400 mL HASTELLOY-C shaker tube. The shaker tube was sealed, evacuated, and charged with Hydrogen Chloride (gas, anhydrous, 7.5 g, 0.2 mol) and heated at 140° C. for 3 hours. The GC analysis of the product mixture indicated complete conversion of $CF_3(CF_2)_5CH_2CH_2SO_2NH(CH_2)_3OH$ to $CF_3(CF_2)_5(CH_2)_2SO_2NH(CH_2)_3Cl$ product.

Example 13

Preparation of $CF_3(CF_2)_5(CH_2)_2SO_2NH(CH_2)_3Cl$ using hydrogen chloride $CF_3(CF_2)_5CH_2CH_2SO_2NH(CH_2)_3OH$ (7 g, 0.014 mol), 1,2-dimethoxyethane (10 g) and tetrabutylphosphonium bromide (0.7 g, 0.002 mol), 0.7 g of silica gel, were charged to the 400 mL HASTELLOY-C shaker tube. The shaker tube was sealed, evacuated, and charged with Hydrogen Chloride (gas, anhydrous, 7.5 g, 0.2 mol) and heated at 140° C. for 3 hours. The GC analysis of the product mixture indicated 87% conversion of $CF_3(CF_2)_5CH_2CH_2SO_2NH(CH_2)_3OH$ to $CF_3(CF_2)_5(CH_2)_2SO_2NH(CH_2)_3Cl$ product.

Example 14

Preparation of $CF_3(CF_2)_5(CH_2)_2SO_2NH(CH_2)_3Cl$ using hydrogen chloride $CF_3(CF_2)_5CH_2CH_2SO_2NH(CH_2)_3OH$ (7 g, 0.014 mol), and 1,2-dimethoxyethane (10 g) were charged to the 400 mL HASTELLOY-C shaker tube. The shaker tube was sealed, evacuated, and charged with Hydrogen Chloride (gas, anhydrous, 7.5 g, 0.2 mol) and heated at 140° C. for 3 hours. The GC analysis of the product mixture indicated 92% conversion of $CF_3(CF_2)_5CH_2CH_2SO_2NH(CH_2)_3OH$ to $CF_3(CF_2)_5(CH_2)_2SO_2NH(CH_2)_3Cl$ product.

Example 15

Preparation of $CF_3(CF_2)_5CH_2CH_2SO_2N(CH_3)(CH_2)_2Cl$ using thionyl chloride $CF_3(CF_2)_5CH_2CH_2SO_2N(CH_3)(CH_2)_2OH$ (50 g, 0.1 mol) and 200 mL of toluene was added to the stirred round bottom flask. Thionyl chloride (SOCl$_2$, 60.8 g, 0.5 mol) was added dropwise, and the resulting reaction mixture was refluxed at 86° C. for 30 min. Solvent was removed under reduced pressure to give crude product (51 g, 98% yield). The resulting crude product was crystallized from hexane. GC/MS (m/z): 44 (100), 69 (61), 77 (38), 119 (30), 131 (35), 140 (55), 156 (23), 169 (33), 213 (12), 263 (13), 327 (21), 390 (66), 435 (14), 454 (100), 455 (100), 456 (48), 484 (21), 486 (8), 502 (1), 504 (0.5).
$^1$H NMR (CDCl$_3$) δ 2.65 (tm, 2H, CH$_2$CF$_2$, J=17.5 Hz), 3.02 (s, 3H, CH$_3$), 3.25 (m, 2H, CH$_2$SO$_2$), 3.58 (t, 2H, CH$_2$N, J=6.3 Hz), 3.68 (t, 2H, CH$_2$Cl, J=6.3 Hz). $^{13}$C NMR (CDCl$_3$) δ 121-105 (m, 6C), 51.51 (b, 1C), 42.69 (1C), 42.69 (t, 1C, CH$_2$CH$_2$CF$_2$, J=4.2 Hz), 41.45 (1C), 26.00 (t, 1C, CH$_2$CF$_2$, J=22.8 Hz).

Reaction 4

Example 16 shows how an embodiment of Reaction 4 was conducted.

Example 16

Preparation of $CF_3(CF_2)_5(CH_2)_2SO_2NH(CH_2)_3OH$ from $CF_3(CF_2)_5(CH_2)_2SO_2Cl$ and $H_2N(CH_2)_3OH$ (3-amino-1-propanol). 3-aminopropan-1-ol (68.2 g, 0.91 mol) and 1,2-dimethoxyethane (276 g) were placed in 1 Liter round bottom flask equipped with mechanical stirring under nitrogen. Solution of $CF_3(CF_2)_5(CH_2)_2SO_2Cl$ (200.1 g, 0.45 mol.), in 1,2-dimethoxyethane (121 g) was added dropwise during 2.5 hours at 20-40° C. while stirring at 350 rpm. The reaction mixture was stirred at 55° C. for 2 h after the addition is completed, and monitored by GC to ensure the complete conversion of $CF_3(CF_2)_5(CH_2)_2SO_2Cl$. The reaction mixture was acidified with $H_3PO_4$ (1.8 g) to pH=5.5, decanted and filtered from solids through a layer of CELITE 545. The solids were washed with 1,2-dimethoxyethane (2×50 g, 1×30 g), and combined filtrate was evaporated in vacuum to obtain 215.2 g of dried product, containing by GC analysis approximately 86 wt % of $CF_3(CF_2)_5CH_2CH_2SO_2NH(CH_2)_3OH$ and 6 wt % of $CF_3(CF_2)_5(CH_2)_2SO_2NH(CH_2)_3Cl$. NMR (CDCl$_3$) δ 1.83 (p, 2H, $CH_2CH_2CH_2$, J=5.9 Hz), 2.64 (tm, 2H, $CH_2CF_2$, J=17.0 Hz), 3.27 (m, 2H, $CH_2SO_2$), 3.34 (m, 2H, $CH_2N$), 3.85 (t, 2H, $CH_2OH$, J=5.5 Hz), 4.95 (1H, broad s).

Example 17

Preparation of $C_6F_{13}CH_2CH_2SO_2NHC_3H_6I$ from $C_6F_{13}CH_2CH_2SO_2NHC_3H_6Cl$ NaI (7.46 g, 0.05 mol) was added to a solution of $C_6F_{13}C_2H_4SO_2NHC_3H_6Cl$ (5 g, 0.01 mol) in MeOH (50 mL). The mixture was refluxed for 18 hours and the solvent was removed to obtain a brown solid product residue. GC analysis indicated complete conversion of starting material into the product. GC/MS (m/z): 58 (16), 69 (11), 77 (9), 119 (4), 127 (3), 131 (6), 156 (6), 169 (12), 213 (2), 232 (3), 263 (3), 277 (4), 327 (8), 376 (8), 440 (54), 468 (100), 576 (2), 595 (0.5).

What is claimed is:

1. A polyfluoroalkylsulfonamido alkyl halide represented by

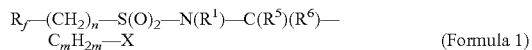
(Formula 1)

wherein:
$R_f$ is chosen from a $C_2$-$C_{12}$ polyfluoroalkyl optionally interrupted by one to four groups chosen from: —O—, —S—, —S(O)—, and —S(O)$_2$—;
n is 2; $R^1$, $R^5$, $R^6$ are independently chosen from hydrogen, $C_1$ to $C_6$ hydroxyalkyl, $C_1$ to $C_6$ halogen substituted alkyl, or a $C_1$ to $C_6$ linear or branched alkyl;
$C_mH_{2m}$ is linear or branched alkyl, and
m is chosen from an integer from 1 to 10; and
X is a halogen selected from the group consisting of Cl, Br, I and mixtures thereof.

2. The polyfluoroalkylsulfonamido alkyl halide of claim 1 wherein
$R_f$ is chosen from $CF_3(CF_2)_5$, or $CF_3(CF_2)_3$;
$R^1$, $R^5$, and $R^6$ are the same and are hydrogen;
n is 2;
m is 2; and
X is chlorine.

3. A method for making the polyfluoroalkylsulfonamido alkyl halide of claim 1 comprising reacting a polyfluoroalkylsulfonic compound with a monoamino alkyl halide, or salt thereof under suitable conditions to make a polyfluoroalkylsulfonamido alkyl halide wherein:
i) the polyfluoroalkylsulfonic compound is represented by

(Formula 3)

wherein Y is chosen from aryloxy, substituted aryloxy, or a halide such as F, Cl, or Br; and
ii) the monoamino alkyl halide or salt thereof is represented by

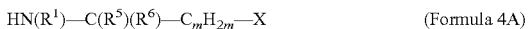
(Formula 4A)

or

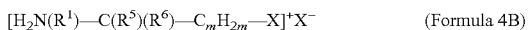
(Formula 4B)

wherein each X is a halogen independently selected from the group consisting of from Cl, Br, I and mixtures thereof.

4. A method for making the polyfluoroalkylsulfonamido alkyl halide of claim 1 comprising reacting a polyfluoroalkylsulfonamido alkyl alcohol with a halogenating agent under suitable conditions to make a polyfluoroalkylsulfonamido alkyl halide wherein the polyfluoroalkylsulfonamido alkyl alcohol is represented by

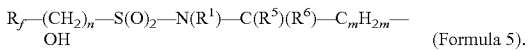
(Formula 5).

5. The method for making the polyfluoroalkylsulfonamido alkyl halide of claim 4 wherein the halogenating agent is selected from the group consisting of HCl, HBr, HI, SOCl$_2$, SOBr$_2$, SOI$_2$, PCl$_5$, PBr$_3$, and PI$_3$.

6. A method for making the polyfluoroalkylsulfonamido alkyl halide of claim 4 wherein the polyfluoroalkylsulfonamido alkyl alcohol is made by reacting a polyfluoroalkylsulfonic compound with an amino alkyl alcohol under suitable conditions to make the polyfluoroalkylsulfonamido compound wherein:
i) the polyfluoroalkylsulfonic compound is represented by

(Formula 3)

Y is chosen from aryloxy, substituted aryloxy, or a halide such as F, Cl, or Br; and
ii) the amino alkyl alcohol is represented by

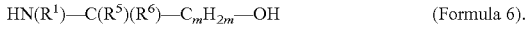
(Formula 6).

* * * * *